United States Patent [19]
Kobayashi

[11] Patent Number: 5,430,509
[45] Date of Patent: Jul. 4, 1995

[54] SCANNING LASER OPHTHALMOSCOPE

[75] Inventor: Koji Kobayashi, Chofu, Japan

[73] Assignee: Kowa Company Ltd., Japan

[21] Appl. No.: 209,566

[22] Filed: Mar. 10, 1994

[30] Foreign Application Priority Data

Mar. 16, 1993 [JP] Japan ............... 5-054477

[51] Int. Cl.⁶ ............................................. A61B 3/10
[52] U.S. Cl. ................................... 351/221; 351/206
[58] Field of Search ............... 351/205, 206, 211, 214, 351/221; 128/745; 356/380

[56] References Cited

U.S. PATENT DOCUMENTS 4,781,453  11/1988  Kobayashi ................. 351/221

Primary Examiner—William L. Sikes
Assistant Examiner—Huy Mai
Attorney, Agent, or Firm—Adams & Wilks

[57] ABSTRACT

A laser beam emitted by a laser light source is scanned in a series of small, high-speed oscillations in a first scanning direction by an acousto-optical deflector, and scanned at a lower frequency in a second direction perpendicular to the first scanning direction by a vibration mirror galvanometer, and scanned at yet a lower frequency in a third direction, parallel to the first direction, by a mirror galvanometer in order to enable high-precision scanning, and is projected onto a prescribed region of an eye. Light reflected by the eye passes, via the mirror galvanometers and, through a confocal optical aperture and is converted to an electrical signal by a photosensor. The signal is then converted by a signal processor to a standard television line format.

52 Claims, 12 Drawing Sheets

SCANNING LASER OPHTHALMOSCOPE

FIELD OF THE INVENTION

The present invention relates to an ophthalmoscope, and more particularly to a scanning laser ophthalmoscope in which a laser beam from a laser light source is projected onto a prescribed part of an eye and scanned in two dimensions, and light reflected from the eye is detected by light receiving means and photoelectrically converted to thereby obtain image information about the eye.

BACKGROUND OF THE INVENTION

In vivo examination of the eye fundus is used not only for ophthalmological purposes but also for diagnosing other disorders that include hypertension, diabetes, and diseases of the cerebral nerves. One technique used for such examinations involves the physician using a device known as the ophthalmoscope to directly observe the eye fundus. In another method that is extensively applied, a special fundus camera is used to record photographs of the fundus on conventional film. The advances made in recent years by electronics have led to the use of optoelectronic transducers such as imaging tubes and the like in place of the photographic film of the conventional fundus camera, whereby eye fundus information is directly obtained in the form of electric signals which can be processed, stored and displayed on a television monitor or the like.

One innovative development in ophthalmology that has attracted attention is that of an electronic ophthalmoscope that utilizes laser scanning techniques. Such a device is known as a scanning laser ophthalmoscope (hereinafter also abbreviated to "SLO"), and is being developed and improved mainly in the U.S., Germany, France and Japan.

With the first SLOs, a laser beam was passed through the center of the pupil and used to scan the eye fundus two-dimensionally, and the light reflected from the fundus through a larger area around the periphery of the pupil was picked up, photoelectrically converted and amplified, whereby with the fundus illuminated at a low brightness it was possible to display a video image of the fundus on a monitor television in real-time with a high S/N ratio (see Reference (1): U.S. Pat. No. 4,213,678 and Applied Optics Vol. 19 (1980) pp 2991 to 2997).

The feasibility of using an active optical element to compensate for the effect of aberration in the optical system of the eye was studied as a way of achieving a major improvement in fundus image resolution, compared to the conventional fundus camera (see Reference (2): DP 3245939, U.S. Pat. No. 4579430, JP-A-59-115024, SPIE Proceedings Vol. 498 (1984) pp 76 to 82).

The adoption of a confocal optical system in the device arrangement was particularly effective for improving picture quality. This eliminated the effect of stray and scattered light and produced a marked improvement in fundus image contrast and resolution (see Reference (3): FP 2555039, JP-A-60-132536, Journal of Optics (Paris) Vol. 15 (1984) pp 425 to 430; Reference (4): U.S. Pat. No. 4764005, JP-A-62-117524, Applied Optics Vol. 26 (1987) pp 1492 to 1499). In such an arrangement, by simultaneously scanning the incident and reflected light beams (double-scanning) and using an optoelectronic detector to acquire and fix reflected light scanning, just the reflected light from a point that is optically conjugate with the fundus of the eye being examined can be detected via a confocal aperture such as a pinhole, enabling the effect of unrequired light scattered by the optical system of the eye to be totally excluded.

The confocal optical system has also been used in attempts to detect three-dimensional sectional shapes of the fundus and anterior chamber by two-dimensional laser beam scanning (X and Y scanning) combined with scanning in the direction of the optical axis (Z scanning) (sec Reference (5): SPIE Proceedings Vol. 1028 (1988) pp 127 to 132).

It has been confirmed that a confocal optical system that uses a slit instead of a pinhole is also a highly effective way of improving the quality of fundus images (see Reference (6): JP-A-64-58237, U.S. Pat. No. 4854692, Measurement Science and Technology Vol. 2 (1991) pp 287 to 292).

More recently still, an apparatus has been developed which represents a major advancement, in that it can provide completely real-time detection and display of uneven configurations in the fundus (see Reference (7): JP-A-1-113605, U.S. Pat. No. 4,900,144, Optics Communications Vol. 87 (1992) pp 9 to 14).

Each of these new ophthalmological devices are highly practical because they enable the fundus image to be observed without using a mydriatic to dilate the pupil, despite the relatively small diameter of the pupil. With these devices, the crystalline lens, the anterior chamber and other such regions can be observed by shifting the focal point of the laser beam from the focal plane, the amount of fluorescent agent that needs to be administered when carrying out fluorography of the eye fundus can be considerably decreased, visual function can be examined during observation of the fundus by modulating the scanning laser beam, and a wide range of precise, microscopic examinations of the fundus are possible, using the monochromatic properties of lasers. SLOs are bringing about major innovations in ophthalmology.

However, a major drawback with such devices is the difficulty of the laser beam deflection control system. In References (1) and (3), for example, two mechanical deflectors (swinging mirrors) arc used to scan the laser beam at a horizontal frequency of some 8 kHz and a vertical frequency of 60 Hz (or 50 Hz). Reference (3) also uses a modified system configuration in which the 8 kHz oscillation rate of the horizontal mirror is doubled to enable tracking at a standard TV horizontal scanning frequency of about 16 kHz.

The rapid wear of the mirror suspension bearings caused by this high mirror oscillation frequency of 8 kHz used in those systems to effect the horizontal scanning has an adverse affect on system durability. Over time, shaft wear and fatigue can result in shaft run-out, deviation, hysteresis and other such variations, which, in the case of a SLO in which image quality depends on beam scanning precision, degrades the reliability of the apparatus itself. Another problem with a mirror oscillating at a scanning frequency above about 8 kHz is that in order to achieve the increased oscillation frequency the mirror has to be no more than 5 mm in diameter, and the deflection angle must not exceed 10 degrees or so, which in the case of an eye fundus image system make it impossible to provide high resolution with a wide field of view.

References (2) and (4) use a mirror galvanometer for the low frequency vertical scanning and a rotating polygonal mirror as the deflector for the horizontal scanning. Systems using a polygonal mirror have good beam scanning high-speed characteristics and linearity, and as they are capable of a deflection angle of 20 degrees or more they are better able to provide high image quality with a wide viewing angle than systems that use high frequency vibration mirrors. For full synchronization with the standard NTSC television scanning system, Reference (4) uses a horizontal scanning frequency of 15.75 kHz and a vertical scanning frequency of 60 Hz. In view of current state of the technology, these scanning frequencies are an eminently good choice, and are also practical with reference to interfacing with peripheral equipment.

However, a problem with achieving a scanning frequency of 15.75 kHz is that of the high speed at which the polygonal mirror has to spin, 37,800 rpm in the case of a mirror with 25 facets. In other words, there is still the problem of durability that arises in the case of a mechanical deflector operating at high frequencies, with parts affected by wear and metal fatigue degrading the precision and shortening the service life of the system. With a polygonal mirror, also, image quality can be degraded by unevenness in the laser beam raster caused by shaft play and slight differences in facet trueness and facet division tolerance, and the mirror is also prone to external vibration. A system that uses high-speed rotation needs large bearings and rotation is restricted to a predetermined direction, which make it difficult to reduce the size of the system. A further drawback is the small size that each facet of the mirror is restricted to, so that the scanning is accompanied by an optical shift of the pupil which, in a confocal optical system, results in a reduction of detection efficiency at the end of scan lines and shading of the images.

To avoid the problems relating to durability, shaft run-out and the like that are inherent to mechanical deflectors, for the horizontal scanning the systems of References (6) and (7) each use a non-mechanical acousto-optical deflector (AOD) having no moving parts. An AOD ensures a long service life and highly stable and precise scanning, and also makes it easier to reduce system size.

However, with an AOD the size of the crystal aperture is limited, and generally there are also limitations on the polarization direction that transmits the light, which make it difficult to configure a perfectly confocal optical system using simultaneous double scanning of the incident beam and light reflected by the fundus. Reference (6) therefore describes use of a modified SLO optical system in which the confocal aperture is a slit. Compared to a non-confocal optical system, one that uses a slit aperture offers a marked improvement in image contrast, and is also advantageous in terms of the design of the system apparatus. Even compared to a pinhole (i.e. round aperture) confocal optical system, a slit does not produce much of a difference when the fundus image is observed using short-wavelength visible light (such as blue, green, yellow). However, when long-wavelength light (such as red and infrared) is used, an image obtained with a SLO that uses a slit aperture is closer to what is obtained with a non-confocal optical arrangement, with the contrast of the retinal vessels in the fundus image slightly lower than that obtained with pinhole aperture.

Thus, a problem of an AOD with a slit aperture confocal optical system, especially when using infrared light, is that to some extent it has limited the contrast in images of retinal vessels. The biggest drawback of an AOD deflector is that when high image resolution is required, the AOD has to be constituted of a special substance such as $TeO_2$ or $PbMoO_4$, formed into a flat, uniform optical medium with a large-diameter aperture. This usually requires that an anamorphic lens, which is complex to adjust, be disposed to the front and rear of the AOD along the optical axis, and the crystal itself is far more costly than small-aperture media.

With reference to the cost aspect, a high-precision, high-speed swinging mirror or polygonal mirror with pneumatic bearings is also very costly. Thus, the matter of cost and problems concerning deflector scanning performance and reliability are probably what has hindered the practical use and spread of SLOs.

Recent years have also seen the realization of high definition television (HDTV), the aim of which is to provide improved resolution and picture quality, and the feasibility of HDTV compatible SLO systems is being studied. However, with an HDTV system having a horizontal scanning frequency of 30 kHz or more, the above-described problems of each type of deflector arrangement would be correspondingly magnified if attempts were made to operate them at such a high frequency. For this reason, despite the interest in the potential of a HDTV compatible SLO, specific working principles or methods for a commercially practicable system have not yet emerged.

The object of this invention is to provide a scanning laser ophthalmoscope having optical scanning means which combines stable, high frequency operation with long service life, high scanning precision and low cost, thereby reducing the overall cost of the system apparatus, a compact system configuration, a confocal optical system that enables high contrast images to be obtained whatever the wavelength of the light used, and which is also fully HDTV adaptable.

SUMMARY OF THE INVENTION

In accordance with the present invention, a laser beam is scanned two-dimensionally using three or more optical scanning means each having a different scanning frequency, which enables the performance conditions required of each scanning means to be reduced, thus providing a durable, low cost deflection control system that is highly stable and precise even at high scanning frequencies. Moreover, the ability to use either a slit or pinhole detection aperture for the confocal optical system provides a large degree of configurability and is also an advantage with respect to improving the contrast and resolution of eye fundus images. Furthermore, although a special scanning pattern is used, as the system is equipped with signal processing means for converting the output of the photosensors to a standard television line scanning system, eye fundus images can be displayed on a standard television and, as such, can be readily adapted for high-definition television.

DETAILED DESCRIPTION OF THE PREFERRED EMBODIMENTS

Figure 1:
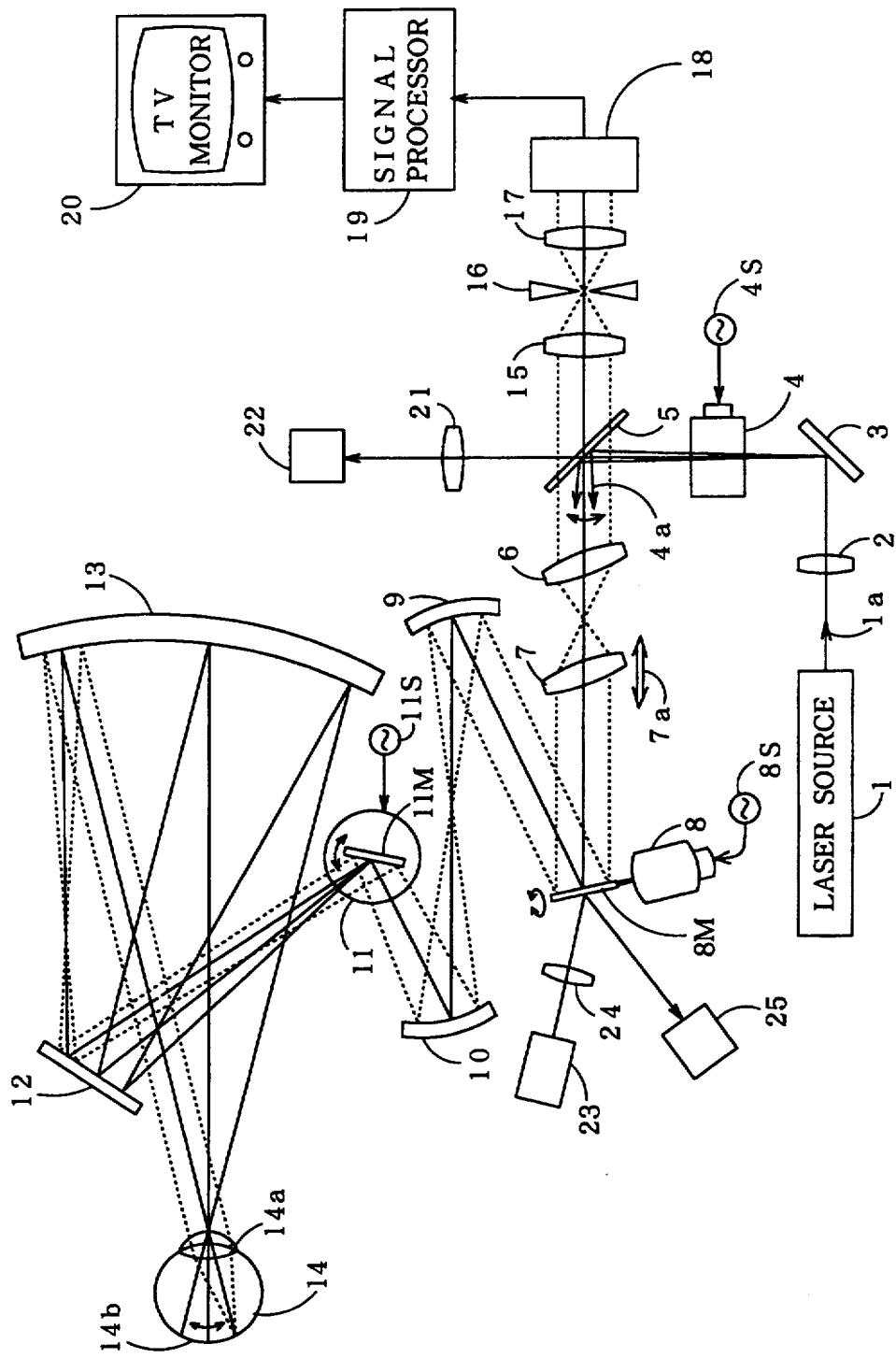
FIG. 1 shows the general arrangement of the optical system of the scanning laser ophthalmoscope apparatus according to the present invention.

FIG. 1 shows the general arrangement of mainly the optical system of the scanning laser ophthalmoscope according to the present invention. In FIG. 1, reference numeral 1 denotes a laser diode (LD), helium-neon (He—Ne), argon (Ar+) or other such laser light source which produces light at any of the wavelengths 780 nm (infrared) or 670 nm (red) in the case of an LD, 632.8 nm (red), 611.9 nm (orange), 594.1 nm (yellow) or 543.5 nm (green) in the case of an He—Ne laser, or 514.5 nm (blue-green) or 488 nm (blue) in the case of an Ar+ laser. Although usually a plurality of laser sources will be used, with beams being combined by a dichroic mirror or the like and a shutter or other such means to enable particular wavelengths to be selected as required, for the purpose 6f this example, one laser source is assumed and illustrated.

A laser beam 1 a emitted by the laser light source 1 is collimated by a lens 2 and reflected by a mirror 3 onto a first scanning means 4. This first scanning means 4 is a non-mechanical optical deflector that can deflect the laser beam at or above a scanning frequency of 5 MHz, such as an AOD or electro-optic deflector (EOD), for example, and is controlled by drive signals from a signal source 4s. With the first scanning means 4, scanning frequency of 7.16 MHz, for example, was selected for overall synchronization of the system with the standard NTSC television scanning system.

Part of the laser beam 4a scanned at high speed in one direction by the first scanning means 4 is reflected by a beam-splitter 5 and is guided via lenses 6 and 7 to a vibration mirror (resonant swinging mirror) 8M provided on a vibration galvanometer 8. Vibration galvanometer 8 is driven from a signal source 8s to use mirror 8M to effect sine wave deflection of the beam. Galvanometer 8 and mirror 8M form a second scanning means that operates at a frequency such as 3.94 kHz, for example, selected based on an overall system consideration of the standard TV scanning system. Scanning by the second scanning means is perpendicular to the scanning direction of the first scanning means.

The raster of the laser beam scanned two-dimensionally by the first scanning means 4 and second scanning means (8 and 8M) is guided by spherical relay mirrors 9 and 10 and further deflected by a mirror galvanometer 11M provided on galvanometer 11. Galvanometer 11 is driven from a signal source 11s to deflect the laser beam in a sawtooth scanning pattern, forming a third scanning means. A scanning frequency of 60 Hz, for example, is selected for the mirror galvanometer 11M, based on a consideration of the standard TV scanning system. Scanning by the third scanning means is perpendicular to the scanning direction of the second scanning means, and therefore parallel to the scanning of the first scanning means.

The raster scan produced by the laser beam being reflected by the mirror galvanometer 11M (i.e. the third scanning means) is reflected by mirror 12 and tilted objective mirror 13 and directed through the pupil 14a of the eye 14 and onto the eye fundus 14b.

Reflected light (shown in the drawing by dotted lines) from the fundus 14b travels back along the same path, going via optical system elements 13, 12, 11, 10, 9, 8, 7 and 6, and is then guided by beam-splitter 5, lens 15 and confocal aperture (detection diaphragm) 16 to photosensor 18. The confocal aperture 16 is located at a point that is an optical conjugate of the fundus focal plane to block unrequired scattered light from within the eye and glare components produced in the optical system, and thereby serves to provide a major improvement in the contrast of the fundus image. Eye fundus reflected light signal components from which stray light components have been eliminated by the confocal aperture 16 are photoelectrically converted to detection signals by the photosensor 18. After being processed by a signal processor 19, the detection signals are input to an image output device 20 such as a TV monitor to display the images of the eye fundus 14b.

The lenses 6 and 7 provided in the light projection/-receiving path are used for focal point adjustment (focus or diopter correction) to correct for nearsightedness, farsightedness, astigmatism or other such vision conditions of the eye being examined. For example, misalignment of the laser beam forcal point caused by refractive differences in the eye can be adjusted for by moving the lens 7 along the optical axis, as indicated by the arrow 7a. To prevent light components reflected by the front and rear surfaces of the lenses 6 and 7 from finding its way to the photosensor 18 and thereby reducing the contrast of fundus images, it is preferable for each of the lenses to be tilted at a slight angle to the optical axis, as shown in FIG. 1. Lenses 6 and 7 can also be used for a fourth scanning means for scanning the beam in a fourth direction. The component of the projection laser beam emitted by laser light source 1 that is transmitted by the beam-splitter 5 goes via lens 21 to a second photosensor 22 where it is photoelectrically converted and used to monitor laser beam intensity.

The back of the vibration mirror 8M constituting the second scanning means is illuminated by a light beam from a light-emitting diode 23 via lens 24, which is reflected onto a third photosensor 25. The third photosensor 25 puts out a signal that is used as a reference signal to control synchronization timing and correct hysteresis accompanying sine wave scanning by the second scanning means.

Figure 2:
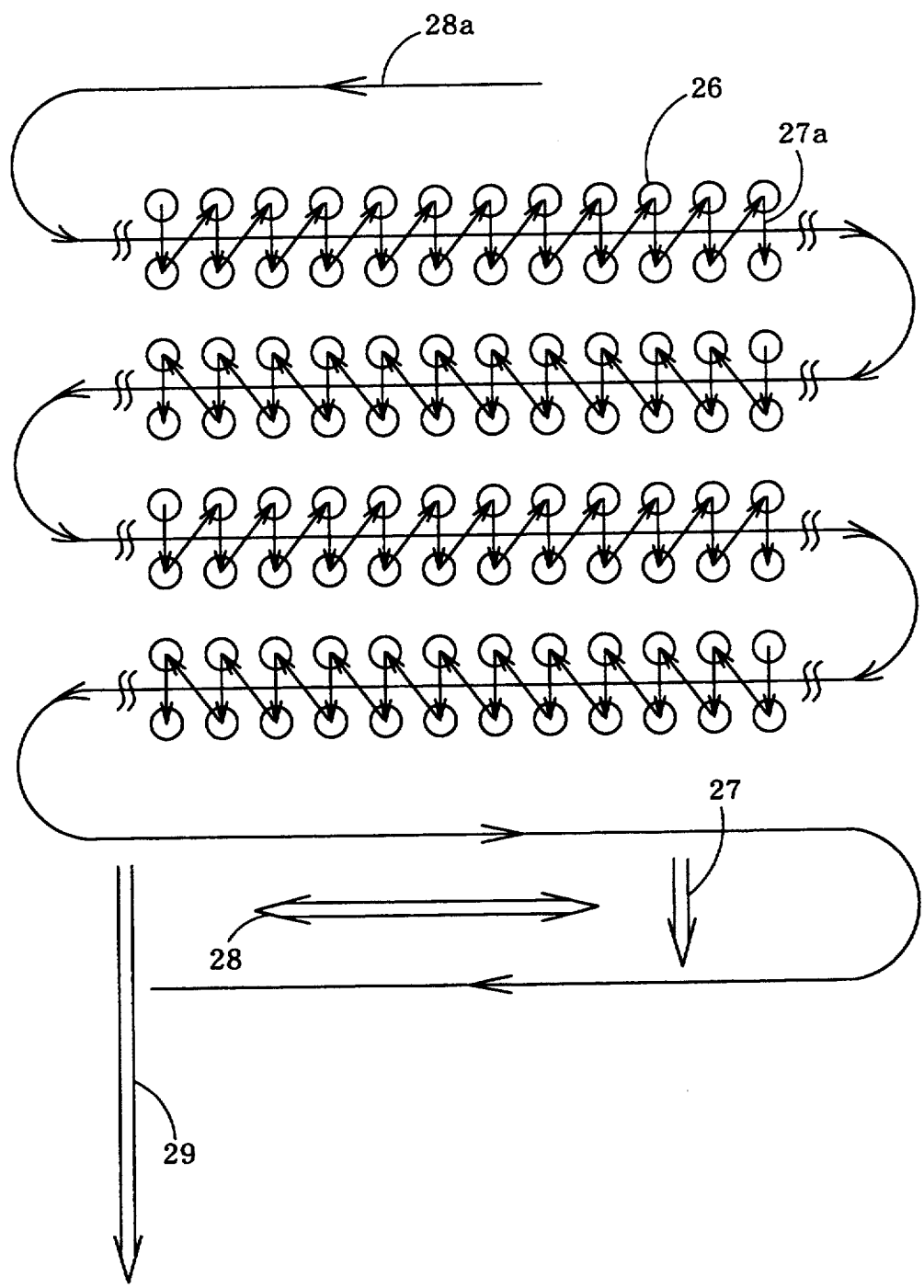
FIG. 2 shows the beam scanning pattern produced by the three scanning means of the apparatus.

FIG. 2 shows the beam scanning pattern produced by the three scanning means in the scanning laser ophthalmoscope of this invention. In FIG. 2, reference numeral 26 denotes a laser beam spot corresponding to a single image pixel, and arrows 27, 28 and 29 denote the respective directions of scanning by the first to third scanning means. 28a denotes the line of the sine wave scanning by the second scanning means; the sawtooth wave shaped linear scan of the third scanning means is downward with reference to the drawing. As shown by arrow 27a indicating the beam scanning by the first scanning means, the high-speed scanning is effected as a series of small oscillations that produce the zigzag pattern shown in the drawing, in accordance with the operation of the three deflectors.

This example assumes that scanning frequencies of 7.16 MHz, 3.94 kHz and 60 Hz have been selected for the first, second and third scanning means. Adjusting the phase timing, a 525 line TV picture raster can be formed thirty times a second. The naked eye cannot tell the difference between the irregular scanning pattern shown in the FIG. 2 and a standard horizontal and vertical scan pattern. However, the signals output by the photosensors have to be processed before they can be used to display the images on a TV monitor. This extremely important function is carried out by the signal processor 19, and will be explained in detail below.

As mentioned, an AOD or an EOD optical deflector is easily capable of operating at a scanning frequency of 7.16 MHz. Of the two, an AOD, which utilizes ultrasonic optical wave diffraction, is preferable, as it does not require a high voltage. However, when two deflectors are used to scan at right-angles and an AOD is used to effect horizontal scanning at a 15.75 kHz frequency corresponding to a TV scanning frequency, as in conventional systems, it has been necessary to use a large aperture AOD to increase the image point resolution, which is extremely costly. In addition, the AOD has to be bracketed by a pair of anamorphic lenses, which are complex to adjust.

In contrast, the AOD forming the first scanning means in the system shown in FIGS. 1 and 2 can be a low cost one with a very small aperture, and anamorphic lenses are not necessary.

A vibration mirror galvanometer capable of sine wave scanning at 3.94 kHz is also readily achievable. With a scanning frequency half that of the frequency used in conventional systems, the durability of the suspension and the reliability of the scanning precision are no longer a problem, and as both the size of the mirror and the deflection angle can be increased, high resolution fundus images can be obtained with a high signal-to-noise ratio, even with the large viewing angle of a confocal system.

Figure 3:
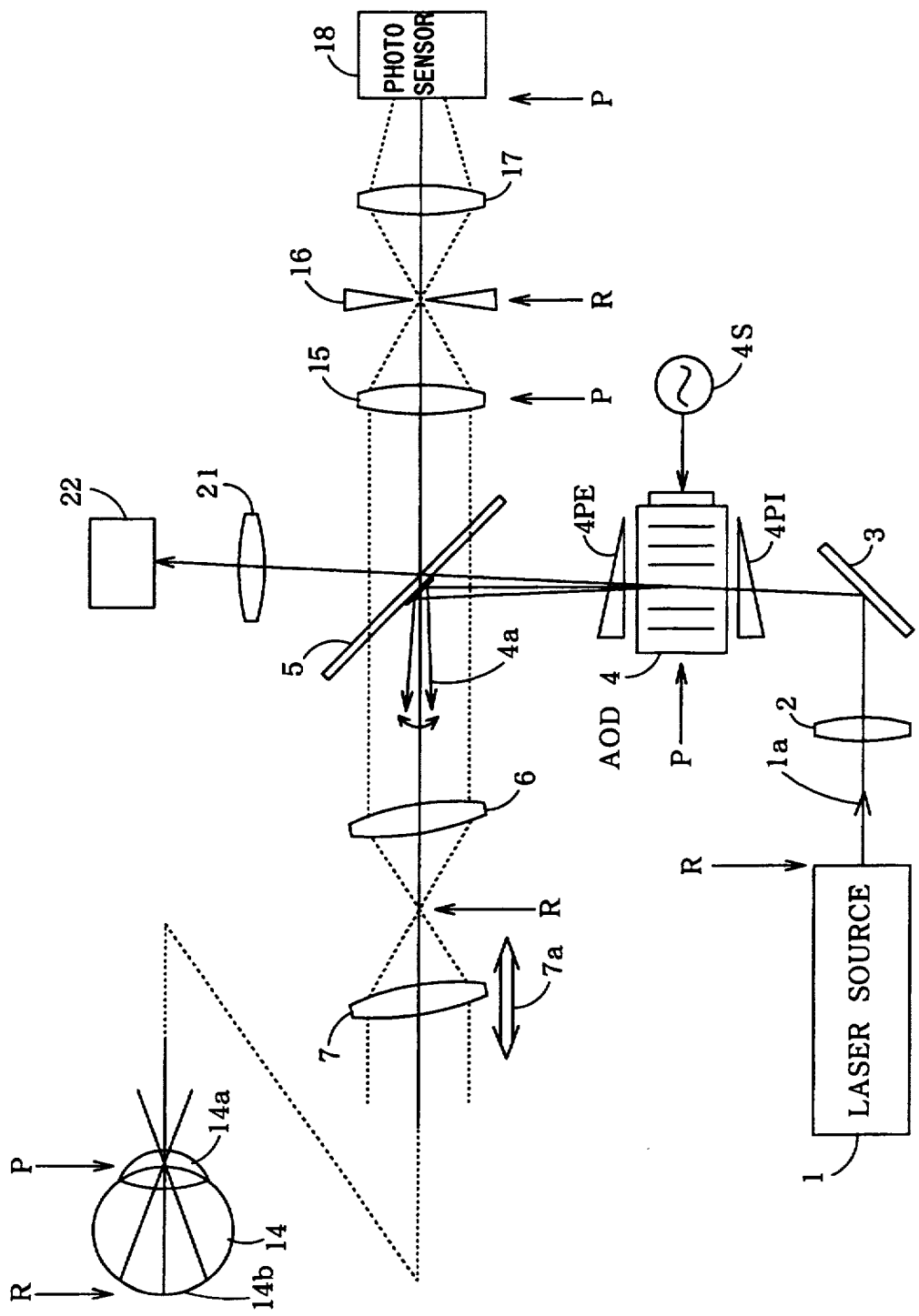
FIG. 3 shows details of the optical system of the apparatus.

FIG. 3 shows details of the first scanning means 4 and beam-splitter 5 portions of the optical system shown in FIG. 1. In the example described here, an AOD is used as the first scanning means 4.

The laser beam is deflected by the AOD 4 in accordance with changes to the lattice constant of the ultrasonic wave diffraction lattice formed in the crystal medium by drive signals from the signal source 4s. By bracketing the AOD 4 by prisms 4PI and 4PE, as shown, the wavelength dependency of the angles of AOD beam incidence and emergence can be fully compensated for.

The beam-splitter 5 is provided as a means of separating the projected and reflected beams against the eye fundus. The beam-splitter can also be used to separate non-deflected zero-order light and first-order deflected light produced by the AOD 4. Specifically, by providing a total-reflection area in the center portion of the beam-splitter 5 to reflect first-order light deflected by the AOD 4, this light can be utilized for projection into the eye 14, via lenses 6 and 7, while zero-order light will be transmitted by the beam-splitter 5 and go via lens 21 to be detected by the second photosensor 22 and used as a laser beam power monitor signal.

In the optical system shown in FIG. 3, the laser beam scanning means has to be located at a position that is optically conjugate with the eye 14 pupil 14a, and the confocal aperture 16 has to be located at a position that is optically conjugate with the eye fundus 14b. In FIG. 3 the former position is indicated by P, for pupillary conjugate, and the latter position by R, for retinal conjugate.

Displacing the beam-splitter 5 by some distance from the pupillary conjugate P on the first scanning means 4 makes it possible to readily separate AOD 4 zero-order and first-order light without a complex optical system. The beam-splitter 5 also serves to separate the beam projected onto the eye fundus from the beam reflected from the fundus.

Reference (4) describes a prior art arrangement in which the optical system uses an acousto-optical modulator (AOM) to modulate the laser beam, with the beam being scanned two-dimensionally by two types of mechanical deflector (a polygonal mirror and a mirror galvanometer). Although at first glance this seems similar to the arrangement shown in FIG. 1 or FIG. 3, the important point is that while in prior art ophthalmoscopes the laser beam may be modulated by an AOM, two-dimensional scanning of the laser beam is always effected by two deflectors arranged at right-angles. In contrast, with the system apparatus according to this embodiment of the invention, two-dimensional scanning is effected by three scanning means, each operating at a different scanning frequency. The explanation made with reference to FIG. 2 shows clearly that the special scanning line format provided by the AOD 4 that constitutes one of these scanning means, has a new and important function that differs completely from the prior art systems.

Figure 4A:
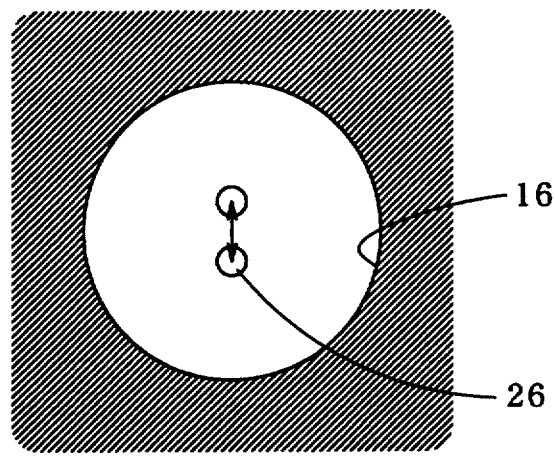
FIGS. 4 (a-c) show the shape and size of the confocal optical aperture in the light receiving system of the apparatus.
Figure 4B:
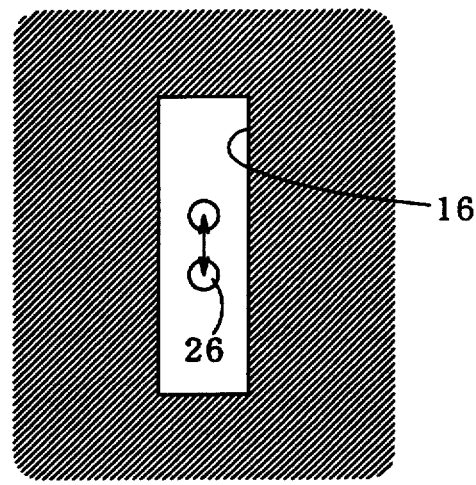
Figure 4C:
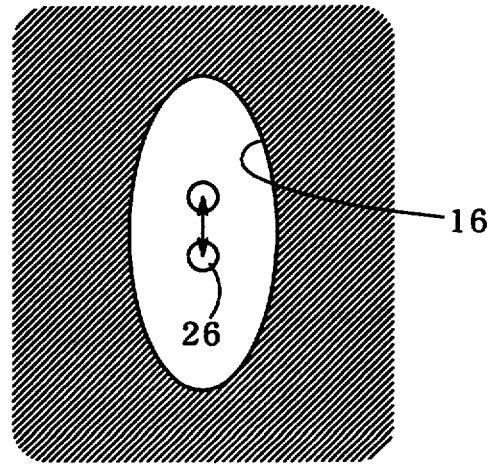

FIGS. 4 (a-c) show the relationship between the size of the incident laser beam spot on the fundus and the size of the confocal optical aperture 16. The reflected light beam from the fundus that is formed on the confocal aperture 16 is scanned in the same direction as the beam scanned by the AOD 4. Thus, if for example a round confocal aperture 16 is used, as shown by FIG. 4 (a), the laser beam spot 26 corresponding to one image pixel will be constantly making small, high-speed movements within the aperture 16. The aperture 16 must therefore be large enough to permit the full range of beam movement while at the same time it has to be small enough to provide an adequately high image contrast. The confocal optical aperture 16 may be rectangular (slit-shaped) as in FIG. 4 (b), or elliptical as in FIG. 4 (c).

A problem in practice is that while the diameter of the laser beam spot projected onto the fundus is around 10 to 20 $\mu$m, the size of the reflected beam may have been increased by the strong optical diffusivity of the fundus tissues. In a unit system, good quality images can be obtained with an aperture size of about 100 to 200 $\mu$m (diameter or width), which will provide sufficient image contrast for retinal vessels, and a high detection S/N ratio and resolution.

With a conventional system using an AOD set to scan at a rate that corresponds to a TV horizontal scan frequency, the confocal aperture has to be a slit. In contrast, the combination of three deflectors used in the system of this invention makes it possible to use round, rectangular, elliptical or other such aperture shapes as required, and it also improves system design flexibility by allowing the most suitable aperture to be selected for the particular laser wavelength and fundus tissue concerned.

Figure 5:
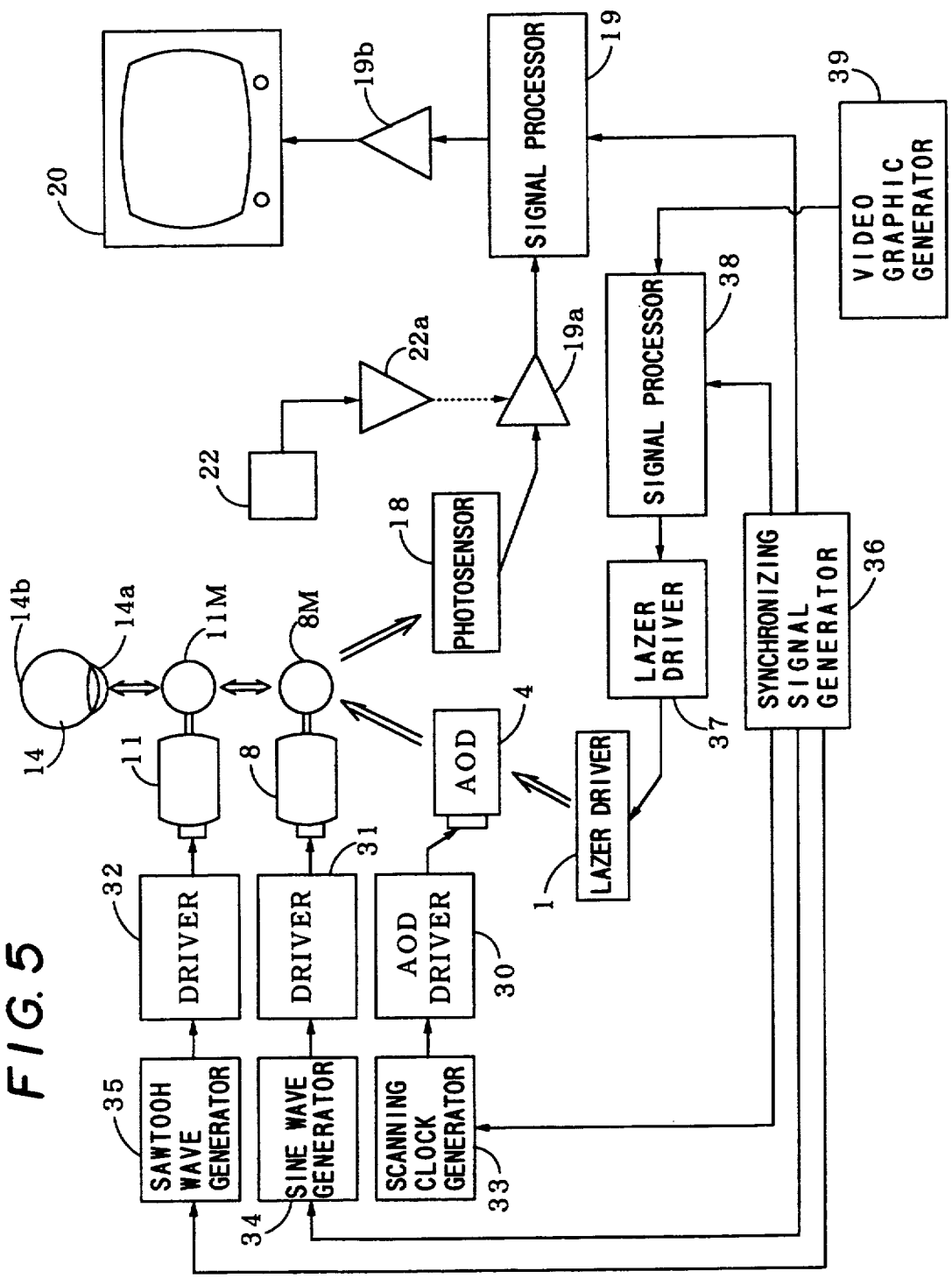
FIG. 5 is a block diagram of the electrical configuration of the apparatus.

FIG. 5 is a block diagram illustrating the electrical configuration of the scanning laser ophthalmoscope according to the present invention. The laser beam emitted by the laser light source 1 is scanned by a trio of optical scanning means consisting of AOD 4, vibration galvanometer 8 and galvanometer 11, which are driven by respective drive circuits 30, 31 and 32 in accordance with respective waveform signals from a scanning clock generating circuit 33, sine wave generating circuit 34 and sawtooth wave generating circuit 35. Synchronized operation of the three scanning means 4, 8 and 11 is controlled by synchronizing signals from a synchronizing signal source 36 applied to the generating circuits 33 to 35.

Light reflected from the fundus 14b passes scanning means 11 and 8 and is converted to an electrical signal by a high sensitivity photosensor 18 such as an avalanche photodiode (APD) or photomultiplier. The photosensor 18 outputs a signal which is amplified to a prescribed level by an amplifier 19a and then input to the signal processor 19 for scanning system conversion. Specifically, the signal processor 19 converts the type of irregular scanning pattern shown in FIG. 2 to a form that enables the fundus image signals to be input to an ordinary TV monitor. The fundus image signals thus processed are amplified to a prescribed level by an amplifier 19b, and then input to an image output device (TV monitor) 20 to thereby provide a real-time display of fundus images as obtained by the laser beam scanning.

In the amplifying of the detection signals from the photosensor 18, using laser beam intensity monitoring signals from the second photosensor 22 and amplifier 22a to control the amplification factor of the amplifier 19a enables clear fundus images to be displayed on the TV monitor with a high S/N ratio, unaffected by any laser beam power variations that may occur.

This scanning laser ophthalmoscope can also use high-speed laser beam modulation to project a vision index image onto the eye fundus for a vision or physiological examination. Laser beam modulation capability can be provided by equipping the laser light source with a special external modulator such as an AOM or the like, or such a function can be added to the first scanning means AOD 4. When possible it is preferable to utilize a laser source that can be directly modulated.

As an example, the arrangement of FIG. 5 includes a drive circuit 37 that can be used to modulate a visible-light laser diode or other such source that can be directly modulated. The drive circuit 37 is connected via signal processor 38 to an external video graphics generator 39 that is able to produce various patterns such as Landholt rings or other such indexes for fixing the eye's vision in a standard TV image format. Because the ophthalmoscope of this invention uses a scanning pattern that is not the same as a TV scanning arrangement, using a standard video signal source for luminance modulation of the laser beam will not be enough to produce a faithful projection of the original video image on the fundus. For this, a signal processor 38 is provided for converting a standard TV image scanning line system to a one that corresponds to the scan pattern produced by the three scanning means 4, 8 and 11. The signal processor 38 is similar to the signal processor 19 in terms of configuration and function, but converts in the opposite direction.

Figure 6:
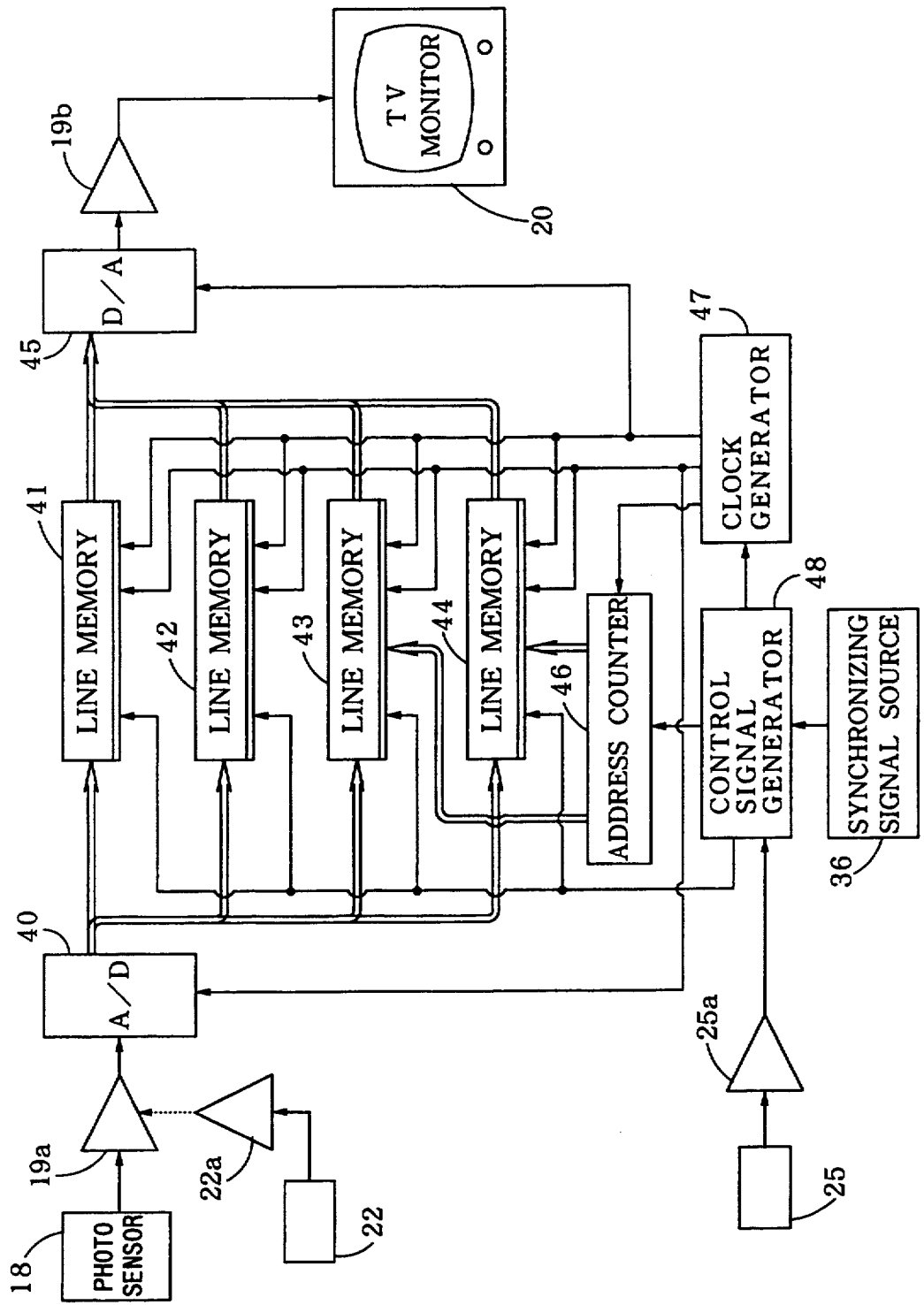
FIG. 6 is a block diagram of the signal processing arrangement used to convert the scanning system in the apparatus.

FIG. 6 is a block diagram that shows the arrangement of the signal processor 19 in further detail. Fundus image detection signals from the photosensor 18 are amplified by the amplifier 19a and converted by A/D converter 40 to 10-bit digital data with a clock rate of 14.3 MHz, for example. The digital data output by the A/D converter 40 is transferred to line memories 41 to 44 in the signal processor 19 corresponding to one scan line of a TV picture, and is then read out of these memories and input to D/A converter 45 for conversion back to analogue signals. The output of the D/A converter 45 is input via amplifier 19b to an image output device 20 such as a TV monitor to provide a real-time display of images from the eye fundus.

The line memories are each able to hold 1024×10-bit pixels, for example, with one line memory corresponding to one scan line. Line memories 41 and 42 are allocated to the outward sine wave movement of the vibration galvanometer 8 and line memories 43 and 44 to the inward movement. Line memories 41 and 24 use a first in, first out (FIFO) scheme, while line memories 43 and 44 require the use of a last in, first out scheme. For this, the memories are connected to an address counter 46 for reversing the coordinates.

The line memories 41 to 44 and the address counter 46 operate in accordance with clock signals from a clock generator 47. Memory read and write timing is controlled by drive signals produced by a control signal generator 48 for each of the digital elements. The control signal generator 48 is operated in accordance with synchronizing signals from a synchronizing signal source 36, and timing signals from the third photosensor 25 and amplifier 25a, utilizing the back of the second scanning means 8M, are used at a reference to control memory writes. Thus, controlling actual changes in vibration mirror oscillation, detected as a reference signal, ensures that any image distortion or the like arising from changes in sine wave oscillation that are temperature based or caused by hysteresis is excluded from the image displayed on the TV monitor.

Figure 7:
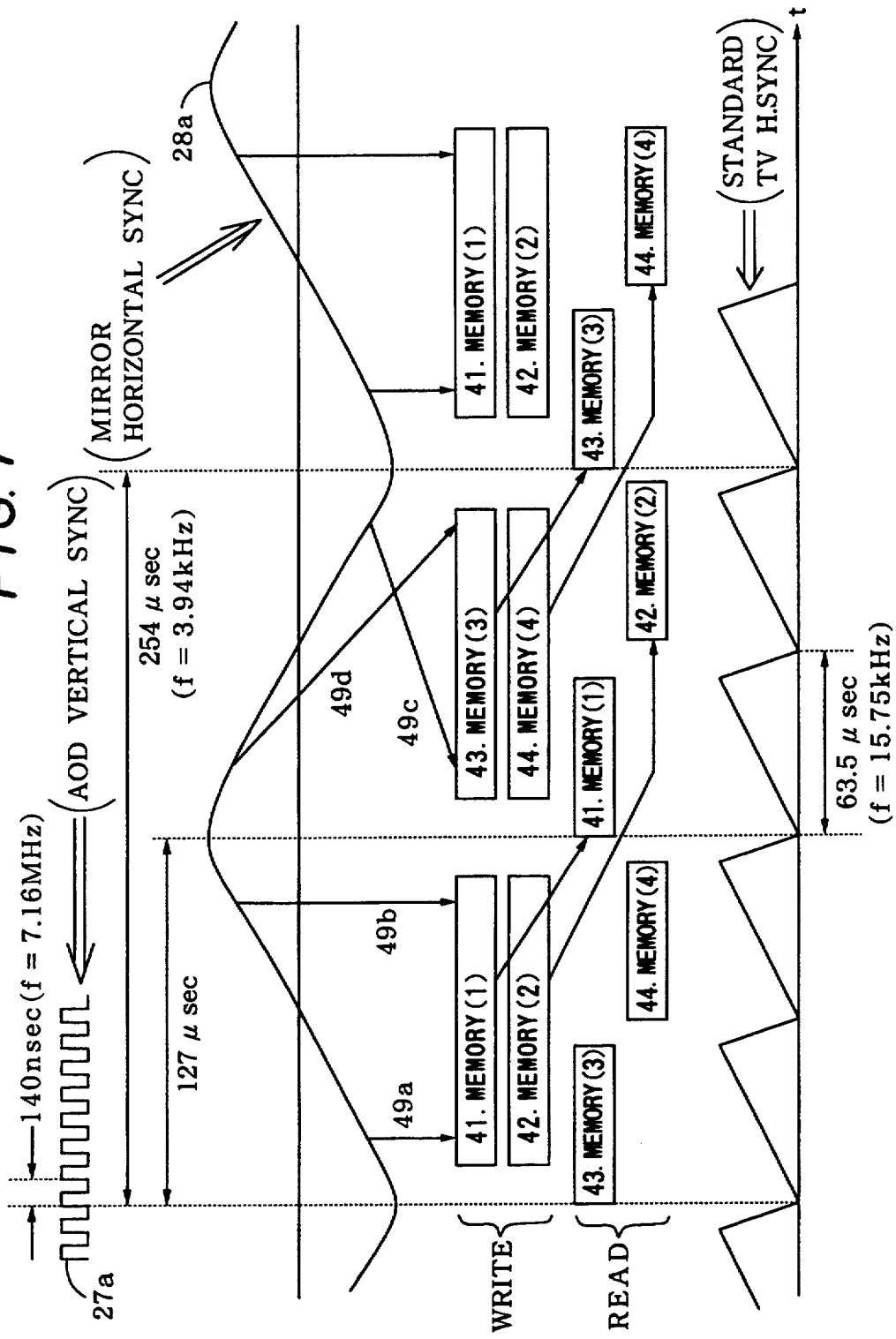
FIG. 7 illustrates the system's line memory based scanning conversion method.
Figure 8A:
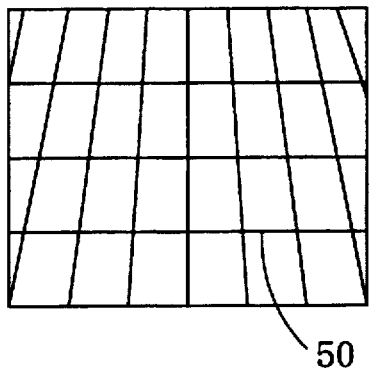
FIGS. 8 (a-e) illustrate the method of correcting image plane distortion in the apparatus.
Figure 8B:
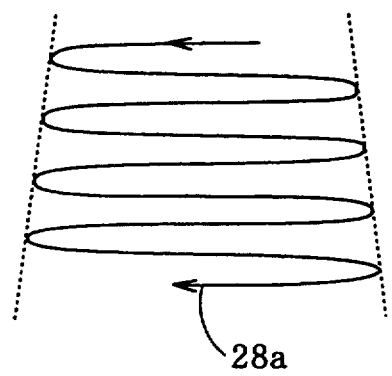
Figure 8D:
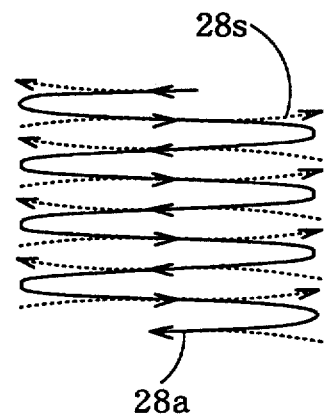
Figure 8C:
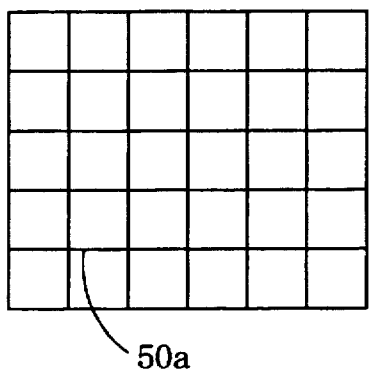
Figure 8E:
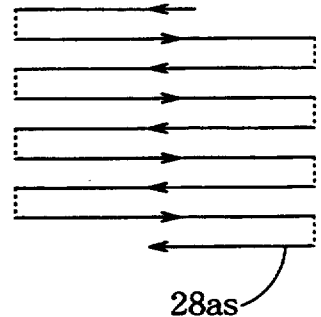

FIG. 7 shows details of how the system's memory section functions. In FIG. 7 the horizontal axis is time, and the path of the scan produced by the second scanning means is shown as a sine wave function 28a. With the scanning frequency of 3.94 kHz used in this example, the scanning period is 254 μsec. With reference to FIG. 7, the small, high-speed deflection scan 27a produced by the first scanning means AOD 4 forms two scan lines for each half period of the sine wave.

Thus, as shown by arrows 49a and 49b, during the outward sine wave movement data is written into line memories 41 and 42, starting with the top address, and is read out in the following half period. As shown by arrows 49c and 49d, during the inward sine wave movement data is written into line memories 43 and 44 starting from the bottom address, and after a sine wave half period the addresses are reversed and the data is read out starting from the top address. The result is that the video signal formed by reading out the memory contents has a period and format that make it exactly equivalent to the scanning signal of a standard TV system.

Reversing memory addresses in the course of sine wave motion to produce an image is known in the prior art. For example, the arrangement of FIG. 3 of FP 2555039 (JP-A-60-132536) (cf. Reference (3)) is similar to that of FIG. 7 of the present application.

However, an important characteristic possessed by this invention but not found in prior art arrangements is that using three or more optical scanning means makes it possible to form a plurality of scanning lines (two, in the present example) within half a horizontal scan period, and that doing this makes it possible to considerably reduce the performance demands imposed on the scanning means used in the system. For example, compared to a conventional system, a much slower scan rate specification can be applied to the mirror of the second scanning means, but when the data is read out from the memory a fundus image signal can be formed that is exactly equivalent to a standard TV signal.

Although conversion of the irregular scanning pattern of the three scanning means has been described with reference to using line memory means for the conversion, field memory or frame memory means can also be used to accomplish the same objective with only slight time delay differences. Despite its complexity, the signal processor can be realized at a low cost, thanks to the advances made in integrated circuit technology.

FIGS. 8 (a–e) illustrate the method of correcting image plane distortion in the system apparatus. When an optical system, such as the one shown in FIG. 1, that uses an objective mirror, such as mirror 13, the offset or tilt of the mirror will give rise to noticeable keystone distortion (or trapezoidal distortion ) in a grid image produced by the optical system, as shown by the grid image 50 in FIG. 8 (a). With a conventional system using an objective mirror, this is not corrected, so to minimize such distortion the objective mirror has to be limited to an tilt that does not exceed about 10 degrees, a constraint that increases the size of the optical system.

In the scanning laser ophthalmoscope according to this invention, however, the sine wave deflection scanning angle of the second scanning means is adjusted to correct the length of the horizontal scan line varying with the vertical displacement of the line, as shown by FIG. 8 (b). It is relatively simple to change the deflection angle of the vibration mirror during scanning, which, as can be seen from the chart image 50a in FIG. 8 (c), provides sufficient correction of the keystone distortion even when a slanted objective mirror is used. Use of this deflection angle control means makes it possible to use a relatively large mirror offset of 10 to 20 degrees, which allows the size of the optical system to be reduced and also increases system design and configuration flexibility.

Sinusoidal scanning has tended to compress the scan lines at each side, degrading the resolution and producing an unnatural rendering of image details. Conventional systems that use sine wave vibration mirrors have had no measures to remedy this.

With the scanning laser ophthalmoscope of this invention, however, the deflection angle DC level of the first scanning means AOD 4 is shifted with respect to the scan line 28a (FIG. 8 (d)) of the second scanning means, which has the booster effect indicated by the dotted line 28s, forming the laser raster 28as in which the scan line spacing is substantially uniform (FIG. 8 (e)). It is difficult to perform this correction with just the second and third scanning means, as it only becomes possible when at least three scanning means are used with the inclusion of the first scanning means AOD. An advantage of thus making the scan line spacing uniform is that it enables a relatively long effective scan period to be set with respect to the direction of vibration mirror scanning.

Figure 9A:
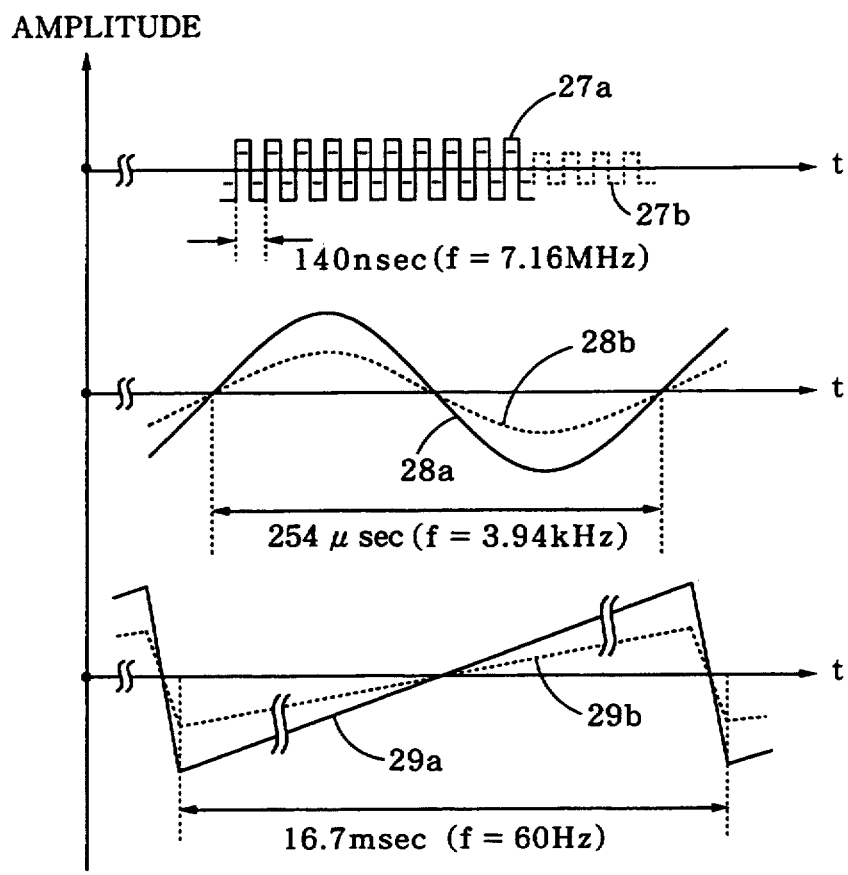
FIGS. 9 (a-b) illustrate the angle of view conversion principle used in the apparatus.

FIGS. 9 (a–b) illustrate an example of an angle of view conversion means in the system apparatus of the invention. FIG. 9 (a) shows the scanline waveforms of the three scanning means, each of which operates at a different scanning frequency. A scanning period (frequency) of 140 Nsec (7.16 MHz) for the first scanning means, 254 μsec (3.94 kHz) for the second scanning means and 16.7 msec (60 Hz) for the third scanning means are assumed.

With respect to the scanning waveforms 27a, 28a and 29a of FIG. 9 (a), the area of the fundus that is scanned for observation is assumed to be region 51a of FIG. 9 (b). In this example, fundus images of papilla 52p, retinal blood vessels 52v and macula lutea 52m are being observed on a TV monitor.

Figure 9B:
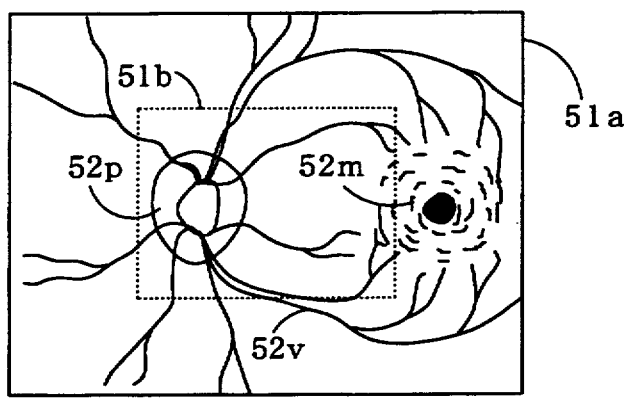

Decreasing the amplitude of the scanning waveform, as shown in FIG. 9 (a) by the dotted lines 27b, 28b and 29b, reduced the size of the scanned region to 51b of FIG. 9(b), which is magnified when displayed on the monitor screen. Thus, adjusting the beam deflection angle of the three scanning means allows the angle of view to be steplessly increased from 50 degrees to 10 degrees without having to incorporate a special variable power optical system.

Figure 10:
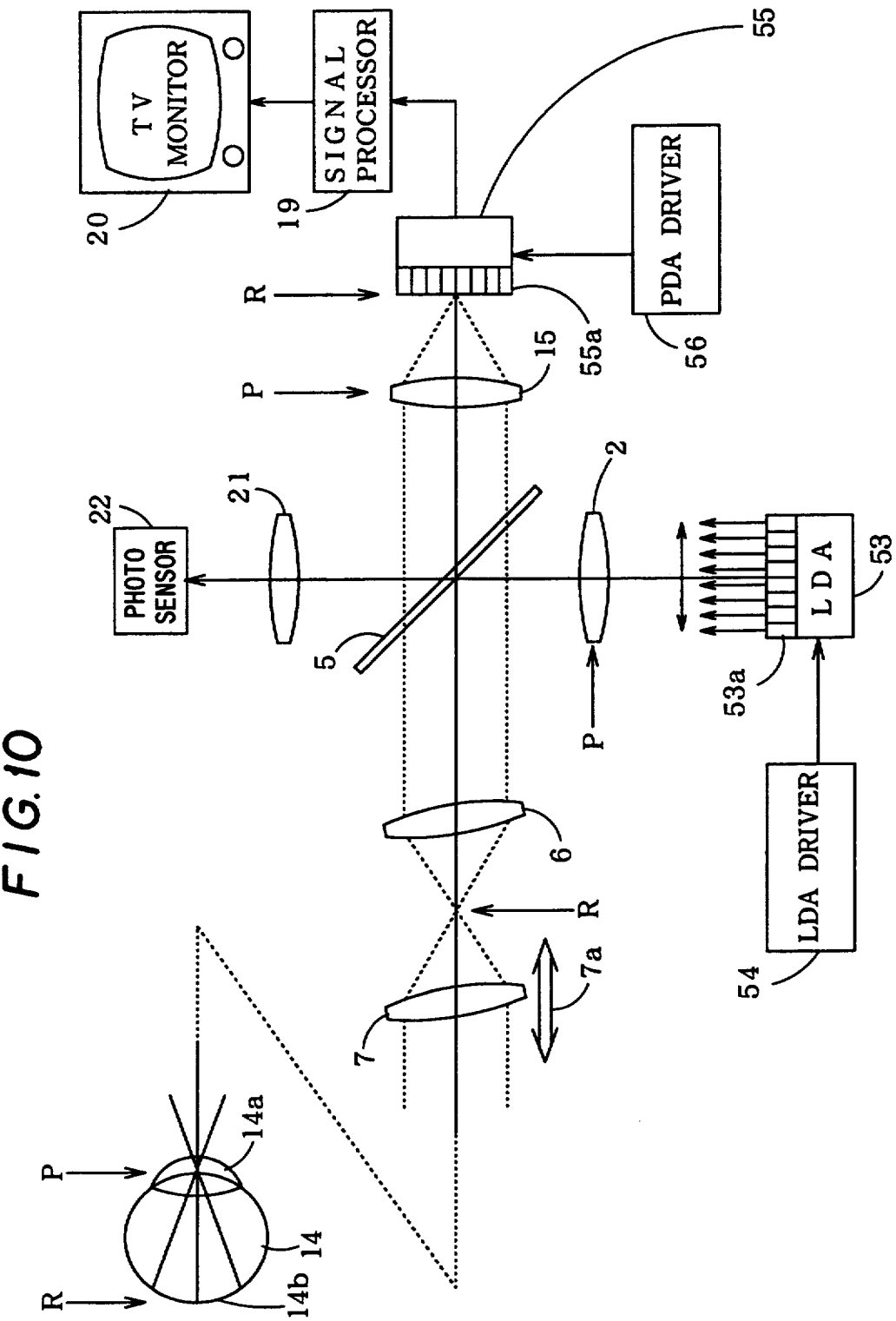
FIG. 10 shows the arrangement of the main components of an optical system according to another embodiment of the invention.

FIG. 10 shows an optical system arrangement according to another embodiment of this invention. In this embodiment, the first scanning means is a laser diode array (LDA) 53. In this example, the LDA is comprised of eight laser diodes, and beam emission is from the front end 53a. The LDA 53 is controlled by a drive circuit 54; the beam switching is used to produce 70 nsec scanning pulses, for example. Thus, in this arrangement the laser light source itself forms the first scanning means.

The scanning laser beam emitted by the LDA 53 is projected onto the eye 14 by the same optical system already described with reference to FIGS. 1 and 2. That is, the beam passes through lens 2 and is reflected through lenses 6 and 7 by beam-splitter 5, and is then guided by the same optical system elements used in the arrangement of FIG. 1. Here too, the second and third scanning means are constituted by two types of mirror.

Reflected light from the fundus 14b travels back along the same path as the incident beam, and via lens 15 forms an image on the light-receiving surface 55a of a photodiode array (hereinafter "PDA") 55. The PDA 55 consists of an array of eight high sensitivity photosensors such as avalanche photodiodes, for example. Each of the eight elements of the PDA 55 has an optically conjugate relationship with each of the corresponding eight elements of the LDA 53. A PDA drive circuit 56 controls the PDA 55, whereby each of the elements outputs light receiving signals as the elements are switched. These signals are passed through the signal processor 19 for conversion to standard video signals, which are input to an image output device 20 such as a TV monitor.

The array elements are arranged at a pitch of about 100 μm, so even with eight such elements, the light emitting (light receiving) parts of the LDA 53 and PDA 55 are very small. In FIG. 10 the elements have been drawn larger to emphasize that they are separate elements.

Figure 11:
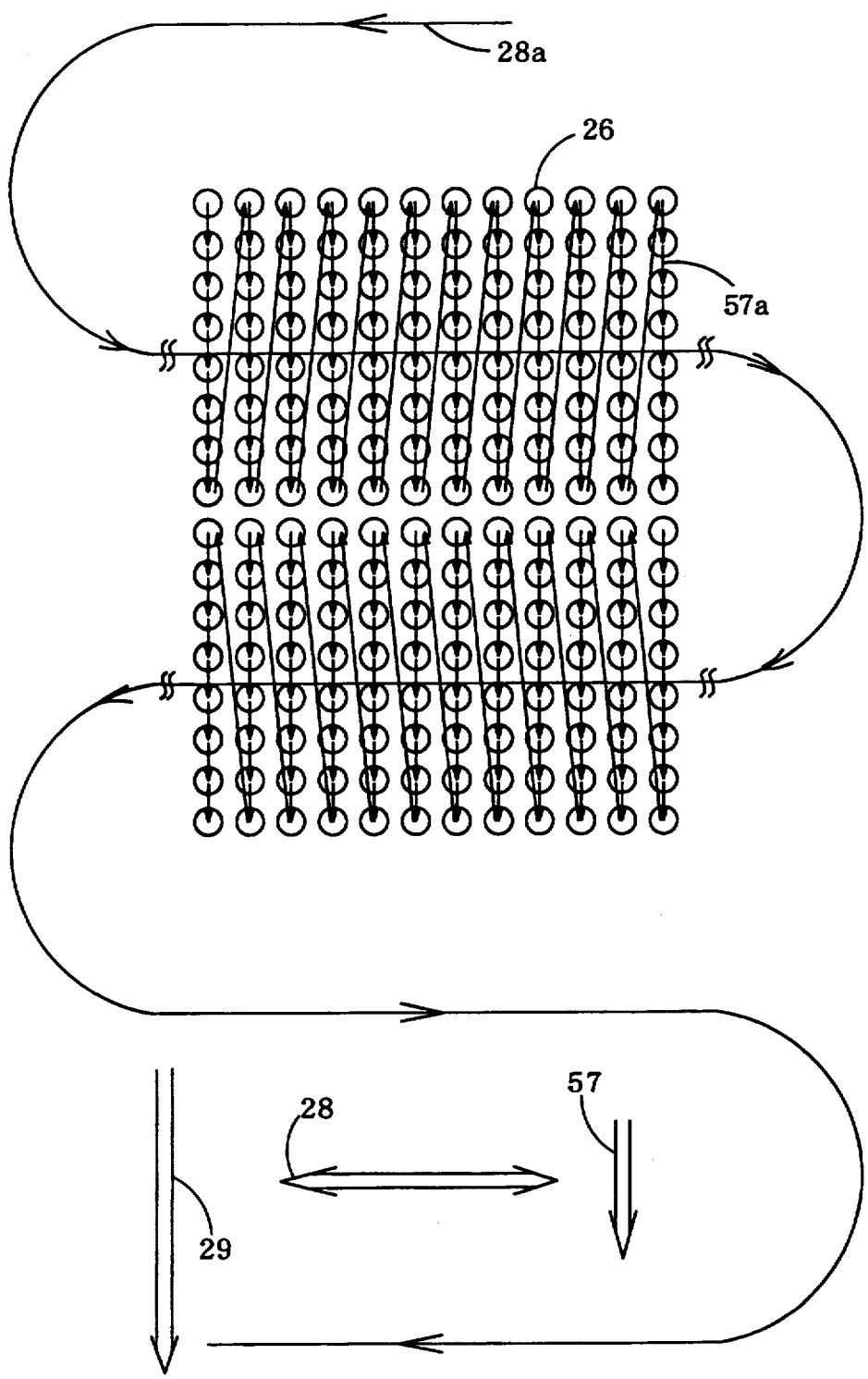
FIG. 11 shows a laser beam scanning pattern produced by the scanning means of the apparatus of the other embodiment.

FIG. 11 shows an example of a laser beam scanning pattern produced by using the three scanning means shown in the arrangement of FIG. 10. In FIG. 11, laser beam spots 26 each correspond to an image pixel, and arrows 57, 28 and 29 show the respective scanning directions of the first to third scanning means. Line 28a indicates the sinusoidal scan path of the second scanning means. Arrows 57a indicate the very high-speed nature of the switched beam scanning of the first scanning means, which with the operation of the three types of deflector produces the scanning pattern shown.

In this example, a scanning frequency (period) of 1.8 MHz (T=560 nsec =70 nsec×8) has been selected for the first scanning means, 980 Hz (1.02 msec) for the second scanning means and 60 Hz (16.7 msec) for the third, so that by using phase alignment of the scanning, a 525-line TV picture can be formed 30 times a second. Also, if the frequencies (periods) of the first and second scanning means are set at 5 MHz (T=200 nsec=25 nsec×8) and 2 kHz (500 μsec), respectively, laser scanning equivalent to over 1000 lines for high definition TV is possible. An LDA switching time as short as 10 nsec per pixel is possible, and a mirror frequency of 1 to 2 kHz is readily realizable, with problems about durability, reliability or resolution. Conversion of the detection signals accompanying the irregular scanning pattern can also be readily realized, based on the principle illustrated by FIGS. 6 and 7, with just slight modifications such as to the memory arrangement of the signal processor 19.

In the scanning pattern shown in FIG. 11 (and in the scanning pattern already described with reference to FIG. 2 and so forth), the vertical movement (shown by the arrow 57a in FIG. 11, or the arrow 27a in FIG. 2) of the beam spot effected by the first scanning means would actually have a diagonal component, owing to the effect of the scanning by the second scanning means. It is to be understood that image distortion produced by such motion can be corrected by adjusting the timing of each pixel controlling readouts from the memories described with reference to FIGS. 6 and 7. Even if there is any diagonal movement of the beam spot, any effect on the video signals obtained by D/A conversion of memory data can be suppressed by adjusting the phase of the corresponding clock. In the drawing the spot movement is depicted as being perfectly vertical simply for descriptive convenience and simplicity.

Figure 12:
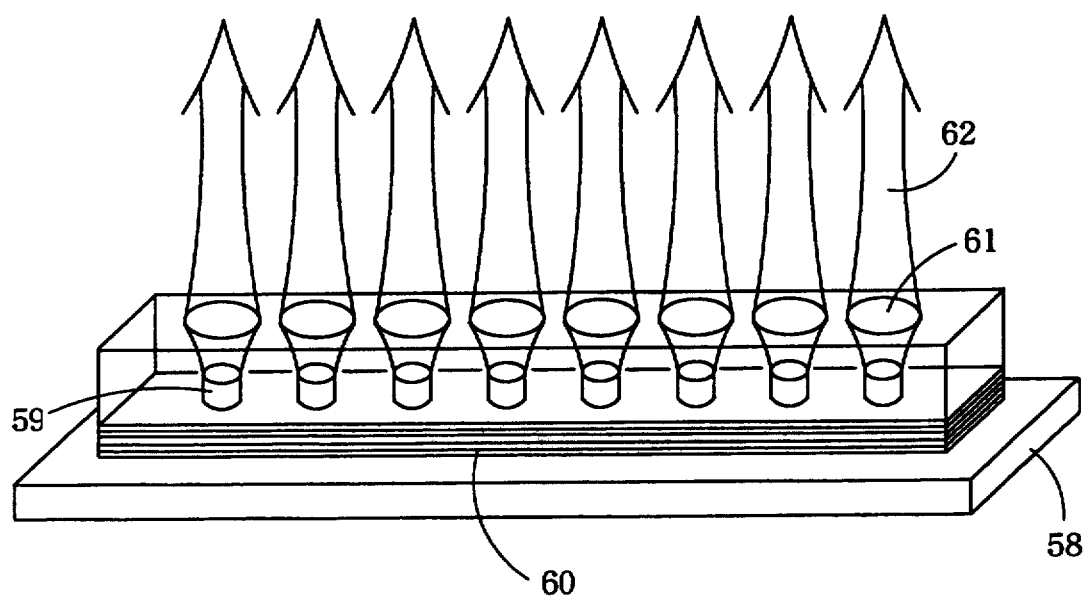
FIG. 12 is a perspective view of the configuration of laser diode array used in the embodiment.

FIG. 12 shows the configuration of the eight-element LDA. The LDA consists of micro-laser chips 59, formed epitaxially on a gallium-arsenide substrate, and a switching microcircuit 60. Reference numeral 61 denotes an array of micro-lenses on the laser chips. These micro-lenses collimate the laser beam 62 emitted by each laser chip. As mentioned, the eight device elements are set very close together, so the whole light emitting section is very small but is fully capable of performing image scanning, using laser switching. With the LDA, the PDA 55 as shown in FIG. 10 can be realized by high sensitivity non-storage sensor arrays similar in structure to the arrangement shown in FIG. 12.

With respect to such light emitting/receiving devices, what is important is the fact that, owing to yield problems, the higher the number of array elements (i.e., the number of pixels) the more difficult it is to manufacture, and even when hey can be manufactured, they are very costly.

If a 1000×1000 pixel laser diode array were to be fabricated and combined with a corresponding 1000×1000 high sensitivity non-storage sensor (the image dissector tube is one such sensor that has been produced), and technology developed whereby the two are synchronized while being switched at high speed to effect the scanning, it would surely be possible to apply to a laser scanning ophthalmoscope. When that happens, previously developed SLOs might well all become obsolete. In this field of scanning technology, the ideal is the elimination of polygonal mirrors, vibration mirrors and other such mechanical moving parts, or the need to use special optical crystals such as AODs and the like, with all deflectors being replaced by semiconductor devices.

However, with respect to light emitting arrays, especially those with a high element count, low-cost fabrication of semiconductor devices capable of producing high quality laser beams of various wavelengths for scanning laser ophthalmoscopic system applications is very difficult, and likely to remain so for some time to come.

Thus, with respect to a practical system apparatus application in which a laser diode array arrangement is used, the ideal is to use it for one of the three typical scanning means, as in the arrangement of FIG. 10, to ensure an overall high level of system performance and reliability. At the same time this solves the problems of durability and scanning precision associated with vibration mirrors and other such means used as the other optical scanning means.

In cases where a polygonal mirror is used as the horizontal scanning means, the technical concept described in the foregoing with reference to the embodiments of this invention can also of course be utilized to reduce the speed (rpm) of the mirror and thereby improve performance factors such as bearing durability and reliability. In a conventional system using a polygonal mirror, a mirror having for example 25 facets has had to rotate at a high-speed 37,800 rpm for compatibility with standard TV systems. In contrast, if the arrangement of this invention is applied, with an AOD, EOD, laser diode array or other such means as the first scanning means, a polygonal mirror as the second scanning means and a mirror galvanometer as the third scanning means, the horizontal scanning polygonal mirror speed can be reduced to 10,000 to 20,000 rpm. This decrease in the speed of the polygonal mirror enables the area of each of the mirror facets to be increased, which by reducing the relative optical shift of the pupil also enhances photodetection efficiency in the confocal optical system.

With the system apparatus according to this invention, also, there is a wide range of optical scanning means options. Depending on the order of the scanning frequency, for example, a waveguide type deflector or optical switching device can be used as the first scanning means, and a vibration mirror utilizing an acoustic or piezoelectric device may be used as the second scanning means. A single vibration mirror can be used that is operated at two frequencies to scan in two directions, which could be regarded as equivalent to two (i.e., the second and third) scanning means.

While the scanning laser ophthalmoscope according to this invention has been described only with reference to its application to ophthalmological examination of the eye fundus, it is to be understood that by using focal plane displacement or the addition of an auxiliary optical system, it can also be used to observe the anterior chamber of the eye, and can also be used for microscopic examination of the corneal epithelium, or to examine the anterior aqueous humor.

It is also to be understood that while the description of optical and electrical systems may have been made with reference to specific structural elements and numerical values, the invention is not limited to such structural elements and numerical values.

Thus, the scanning laser ophthalmoscope according to this invention uses three or more optical scanning means, each with a different scanning frequency, for two-dimensional laser beam scanning, which enables the scanning frequency, resolution, scanning stability, reliability and other such performance conditions required of each of the scanning means to be made considerably less rigorous, ensuring a laser scanning system compatible with standard TV systems that provides high scanning precision and stability and is also highly durable. Although three scanning means are used, because the type of costly horizontal scanning means used by conventional systems to achieve both high scanning frequency and high resolution are not needed, the system can be made less costly, more reliable and more compact.

Moreover, the ability to configure the confocal optical system with a round or slit-shaped detection aperture increases system design flexibility, and is also an advantage with respect to improving the contrast and resolution of eye fundus images.

Furthermore, although a special laser beam scanning pattern is used, the system is equipped with signal processing means for converting the output signals of the photosensors to a standard television raster system, which permits real-time observation of fundus images on a standard television. By incorporating a signal processor for converting picture signals from a standard video signal source to a form that provides compatibility with the system's non-standard laser beam scanning format, it becomes possible to use laser beam luminance modulation to project a vision index image onto the eye fundus for a vision or physiological examination. Also, as the laser beam scanning system can be operated at high scanning frequencies and the number of scan lines can be readily increased, the system can also be adapted to high definition television, and as such has good future upgrade potential.

When an AOD is used as the first scanning means, a vibration mirror as the second scanning means and a mirror galvanometer as the third scanning means, distortion caused by the tilt of the objective mirror can be corrected by controlling the deflection angle of the vibration mirror, and raster distortion accompanying the sinusoidal oscillation can be corrected by controlling the deflection angle of the AOD. Moreover, varying the beam deflection angle of the AOD, vibration mirror and mirror galvanometer enables the fundus viewing angle to be varied without incorporating a special variable power optical system, and also facilitates optical system design and adjustment.

If a laser diode array is used to form the first scanning means, an array with a relatively small number of elements can be utilized, and it also becomes possible to greatly reduce the scanning frequency of the vibration mirror used as the second scanning means, and as such serves to improve scanning precision and increase durability.

What is claimed is:

1. A scanning laser ophthalmoscope in which a laser beam from a laser light source is projected onto a prescribed part of an eye and scanned in two dimensions, and light reflected from the eye is detected and photoelectrically converted by light receiving means to thereby obtain image information on the eye, comprising:

three or more optical scanning means with different scanning frequencies for two-dimensionally scanning a laser beam from a laser light source;

light receiving means for detecting and photoelectrically converting light from one or more of the optical scanning means reflected by the eye, via a prescribed detection aperture; and signal processing means for converting a detection signal obtained from the light receiving means to a standard television vertical and horizontal scanning line system corresponding to a laser beam scanning pattern obtained with the three or more optical scanning means.

2. A scanning laser ophthalmoscope according to claim 1, in which the detection aperture is located at a position that is optically conjugate with the laser beam focal point in the eye, and is formed in a prescribed shape around a region in which the laser beam focal point moves in accordance with the laser beam scanning pattern of the optical scanning means.

3. A scanning laser ophthalmoscope according to claim 1, in which the laser beam scanning pattern formed by all of the optical scanning means is a two-dimensional zig-zag pattern formed by scanning the laser beam in a second direction perpendicular to a first scanning direction while the beam makes small oscillations along the first scanning direction, and scanning the laser beam in a third direction parallel to the first scanning direction.

4. A scanning laser ophthalmoscope according to claim 1, in which the signal processing means for converting a detection signal obtained from the light receiving means to a standard television scanning line system consists of an A/D converter for performing analogue-to-digital conversion of the detection signal, a memory for storing digital data output by the A/D converter, control means for controlling the writing of data to, and readout of data from, the memory, and a D/A converter for performing digital-to-analogue conversion of digital data read out of the memory.

5. A scanning laser ophthalmoscope according to claim 1 further comprising optical focal adjustment means for moving the laser beam focal point in the eye.

6. A scanning laser ophthalmoscope according to claim 5, in which the focus adjustment means is a slanted lens that can be moved along the path of the laser beam.

7. A scanning laser ophthalmoscope in which a laser beam from a laser light source is projected onto a prescribed part of an eye and scanned in two dimensions, and light reflected from the eye is detected and photoelectrically converted by light receiving means to thereby obtain image information on the eye, comprising:

first optical scanning means for scanning a laser beam from a laser light source in one direction at a prescribed frequency;

second optical scanning means for scanning the laser beam in a direction that is perpendicular to the scanning direction of the first optical scanning means at a frequency that is lower than above said frequency;

third optical scanning means for scanning the laser beam in a direction that is perpendicular to the scanning direction of the first or second optical scanning means at a frequency that is lower than either of above said frequencies;

light receiving means for detecting and photoelectrically converting light from one or more of the first, second, and third optical scanning means reflected by the eye, via a prescribed detection aperture; and signal processing means for converting a detection signal obtained from the light receiving means to a standard television vertical and horizontal scanning line system corresponding to a laser beam scanning pattern obtained with the first, second, and third optical scanning means.

8. A scanning laser ophthalmoscope according to claim 7, in which the detection aperture is located at a position that is optically conjugate with the laser beam focal point in the eye, and is formed in a prescribed shape around a region in which the laser beam focal point moves in accordance with the laser beam scanning pattern of the optical scanning means.

9. A scanning laser ophthalmoscope according to claim 7, in which the laser beam scanning pattern formed by all of the optical scanning means is a two-dimensional zig-zag pattern formed by scanning the laser beam in a second direction perpendicular to a first scanning direction while the beam makes small oscillations along the first scanning direction, and scanning the laser beam in a third direction parallel to the first scanning direction.

10. A scanning laser ophthalmoscope according to claim 7 in which the signal processing means for converting a detection signal obtained from the light receiving means to a standard television scanning line system consists of an A/D converter for performing analogue-to-digital conversion of the detection signal, a memory for storing digital data output by the A/D converter, control means for controlling the writing of data to, and readout of data from, the memory, and a D/A converter for performing digital-to-analogue conversion of digital data read out of the memory.

11. A scanning laser ophthalmoscope according to claim 7, further comprising optical focal adjustment means for moving the laser beam focal point in the eye.

12. A scanning laser ophthalmoscope according to claim 11, in which the focus adjustment means is a slanted lens that can be moved along the path of the laser beam.

13. A scanning laser ophthalmoscope in which a laser beam from a laser light source is projected onto a prescribed part of an eye and scanned in two dimensions, and light reflected from the eye is detected and photoelectrically converted by light receiving means to thereby obtain image information on the eye, comprising:

an acousto-optical deflector for scanning a laser beam from a laser light source in one direction at a prescribed frequency;

a vibration mirror galvanometer for scanning the laser beam in a direction that is perpendicular to the scanning direction of the acousto-optical deflector at a frequency that is lower than above said frequency;

a mirror galvanometer for scanning the laser beam in a direction that is perpendicular to the scanning direction of the vibration mirror galvanometer at a frequency that is lower than either of above said frequencies;

light beam separating means disposed on the light path between the acousto-optical deflector and the vibration mirror galvanometer for separating an illuminating beam projected at the eye from a beam reflected from the eye;

light receiving means for detecting and photoelectrically converting light from the two mirror galvanometers and the light beam separating means reflected by the eye, via a prescribed detection aperture; and signal processing means for converting a detection signal obtained from the light receiving means to a standard television vertical and horizontal scanning line system corresponding to a laser beam scanning pattern obtained with the three optical scanning means.

14. A scanning laser ophthalmoscope according to claim 13, in which the detection aperture is located at a position that is optically conjugate with the laser beam focal point in the eye, and is formed in a prescribed shape around a region in which the laser beam focal point moves in accordance with the laser beam scanning pattern of the optical scanning means.

15. A scanning laser ophthalmoscope according to claim 13, in which the laser beam scanning pattern formed by all of the optical scanning means is a two-dimensional zig-zag pattern formed by scanning the laser beam in a second direction perpendicular to a first scanning direction while the beam makes small oscillations along the first scanning direction, and scanning the laser beam in a third direction parallel to the first scanning direction.

16. A scanning laser ophthalmoscope according to claim 13, in which the signal processing means for converting a detection signal obtained from the light receiving means to a standard television scanning line system consists of an A/D converter for performing analogue-to-digital conversion of the detection signal, a memory for storing digital data output by the A/D converter, control means for controlling the writing of data to, and readout of data from, the memory, and a D/A converter for performing digital-to-analogue conversion of digital data read out of the memory.

17. A scanning laser ophthalmoscope according to claim 13, further comprising optical focal adjustment means for moving the laser beam focal point in the eye.

18. A scanning laser ophthalmoscope according to claim 17, in which the focus adjustment means is a slanted lens that can be moved along the path of the laser beam.

19. A scanning laser ophthalmoscope according to claim 13, in which a prism is provided in front of and behind the acousto-optical deflector to correct the wavelength dependence of the angle of incidence and angle of emergence of the beam with respect to the deflector.

20. A scanning laser ophthalmoscope according to claim 13, in which the light beam separation means separates zero-order and first-order diffracted light from the acousto-optical deflector.

21. A scanning laser ophthalmoscope according to claim 20, in which the zero-order light separated by the light beam separation means is used to monitor the power of the laser beam.

22. A scanning laser ophthalmoscope in which a laser beam from a laser light source is projected onto a prescribed part of an eye and scanned in two dimensions, and light reflected from the eye is detected and photoelectrically converted by light receiving means to thereby obtain image information on the eye, comprising:
- non-mechanical optical scanning means for scanning a laser beam from a laser light source in one direction at a prescribed frequency;
- a vibration mirror galvanometer for scanning the laser beam in a direction that is perpendicular to the scanning direction of the non-mechanical optical scanning means at a frequency that is lower than above said frequency;
- synchronous detection means for detecting synchronously with the scanning of the vibration mirror galvanometer;
- a mirror galvanometer for scanning the laser beam in a direction that is perpendicular to the scanning direction of the vibration mirror galvanometer at a frequency that is lower than either of above said frequencies;
- light receiving means for detecting and photoelectrically converting light from the two mirror galvanometers reflected by the eye, via a prescribed detection aperture; and
- signal processing means for converting a detection signal obtained from the light receiving means to a standard television vertical and horizontal scanning line system corresponding to a laser beam scanning pattern obtained with the three optical scanning means, and in accordance with a control signal from the synchronous detection means.

23. A scanning laser ophthalmoscope according to claim 22, in which the detection aperture is located at a position that is optically conjugate with the laser beam focal point in the eye, and is formed in a prescribed shape around a region in which the laser beam focal point moves in accordance with the laser beam scanning pattern of the optical scanning means.

24. A scanning laser ophthalmoscope according to claim 22, in which the laser beam scanning pattern formed by all of the optical scanning means is a two-dimensional zig-zag pattern formed by scanning the laser beam in a second direction perpendicular to a first scanning direction while the beam makes small oscillations along the first scanning direction, and scanning the laser beam in a third direction parallel to the first scanning direction.

25. A scanning laser ophthalmoscope according to claim 22, in which the signal processing means for converting a detection signal obtained from the light receiving means to a standard television scanning line system consists of an A/D converter for performing analogue-to-digital conversion of the detection signal, a memory for storing digital data output by the A/D converter, control means for controlling the writing of data to, and readout of data from, the memory, and a D/A converter for performing digital-to-analogue conversion of digital data read out of the memory.

26. A scanning laser ophthalmoscope according to claim 22, further comprising optical focal adjustment means for moving the laser beam focal point in the eye.

27. A scanning laser ophthalmoscope according to claim 26, in which the focus adjustment means is a slanted lens that can be moved along the path of the laser beam.

28. A scanning laser ophthalmoscope according to claim 22, in which the synchronous detection means uses light reflected by the reverse side of the vibration mirror galvanometer to perform synchronous detection.

29. A scanning laser ophthalmoscope according to claim 22, in which the signal output by the synchronous detection means is used to correct hysteresis accompanying the sine wave scanning of the vibration mirror galvanometer.

30. A scanning laser ophthalmoscope in which a laser beam from a laser light source is projected onto a prescribed part of an eye and scanned in two dimensions, and light reflected from the eye is detected and photoelectrically converted by light receiving means to thereby obtain image information on the eye, comprising:
- light intensity modulating means for modulating the intensity of a laser beam from a laser light source;
- three or more optical scanning means with different scanning frequencies for two-dimensionally scanning a laser beam from a laser light source;
- light receiving means for detecting and photoelectrically converting light from one or more of the optical scanning means reflected by the eye, via a prescribed detection aperture;
- signal processing means for converting a detection signal obtained from the light receiving means to a standard television vertical and horizontal scanning line system corresponding to a laser beam scanning pattern obtained with the three or more optical scanning means;
- a video signal source that generates a prescribed video pattern for visual examination purposes; and
- signal processing means that in accordance with a laser beam scanning pattern obtained with the optical scanning means converts a standard video signal output from the video signal source to a control signal that can be supplied to the light intensity modulating means.

31. A scanning laser ophthalmoscope according to claim 30, in which the detection aperture is located at a position that is optically conjugate with the laser beam focal point in the eye, and is formed in a prescribed shape around a region in which the laser beam focal point moves in accordance with the laser beam scanning pattern of the optical scanning means.

32. A scanning laser ophthalmoscope according to claim 30, in which the laser beam scanning pattern formed by all of the optical scanning means is a two-dimensional zig-zag pattern formed by scanning the laser beam in a second direction perpendicular to a first scanning direction while the beam makes small oscillations along the first scanning direction, and scanning the laser beam in a third direction parallel to the first scanning direction.

33. A scanning laser ophthalmoscope according to claim 30, in which the signal processing means for converting a detection signal obtained from the light receiving means to a standard television scanning line system consists of an A/D converter for performing analogue-to-digital conversion of the detection signal, a memory for storing digital data output by the A/D converter, control means for controlling the writing of data to, and readout of data from, the memory, and a D/A converter for performing digital-to-analogue conversion of digital data read out of the memory.

34. A scanning laser ophthalmoscope according to claim 30, further comprising optical focal adjustment means for moving the laser beam focal point in the eye.

35. A scanning laser ophthalmoscope according to claim 34, in which the focus adjustment means is a slanted lens that can be moved along the path of the laser beam.

36. A scanning laser ophthalmoscope in which a laser beam from a laser light source is projected onto a prescribed part of an eye and scanned in two dimensions, and light reflected from the eye is detected and photoelectrically converted by light receiving means to thereby obtain image information on the eye, comprising:
- three or more optical scanning means with different scanning frequencies for two-dimensionally scanning a laser beam from a laser light source;
- a tilted objective mirror for projecting a scanning laser beam obtained with the optical scanning means at an eye;
- control means that controls the deflection angle of one or more of the optical scanning means to correct optical aberration produced by the tilted objective mirror;
- control means that corrects raster distortion arising from sine wave oscillation in one of the optical scanning means by adjusting the deflection angle of an optical scanning means having a scanning frequency higher than the sine wave oscillation frequency;
- light receiving means for detecting and photoelectrically converting light from one or more of the optical scanning means reflected by the eye, via a prescribed detection aperture; and
- signal processing means for converting a detection signal obtained from the light receiving means to a standard television vertical and horizontal scanning line system corresponding to a laser beam scanning pattern obtained with the three or more optical scanning means.

37. A scanning laser ophthalmoscope according to claim 36, in which the detection aperture is located at a position that is optically conjugate with the laser beam focal point in the eye, and is formed in a prescribed shape around a region in which the laser beam focal point moves in accordance with the laser beam scanning pattern of the optical scanning means.

38. A scanning laser ophthalmoscope according to claim 36, in which the laser beam scanning pattern formed by all of the optical scanning means is a two-dimensional zig-zag pattern formed by scanning the laser beam in a second direction perpendicular to a first scanning direction while the beam makes small oscillations along the first scanning direction, and scanning the laser beam in a third direction parallel to the first scanning direction.

39. A scanning laser ophthalmoscope according to claim 36, in which the signal processing means for converting a detection signal obtained from the light receiving means to a standard television scanning line system consists of an A/D converter for performing analogue-to-digital conversion of the detection signal, a memory for storing digital data output by the A/D converter, control means for controlling the writing of data to, and readout of data from, the memory, and a D/A converter for performing digital-to-analogue conversion of digital data read out of the memory.

40. A scanning laser ophthalmoscope according to claim 36, further comprising optical focal adjustment means for moving the laser beam focal point in the eye.

41. A scanning laser ophthalmoscope according to claim 40, in which the focus adjustment means is a slanted lens that can be moved along the path of the laser beam.

42. A scanning laser ophthalmoscope in which a laser beam from a laser light source is projected onto a prescribed part of an eye and scanned in two dimensions, and light reflected from the eye is detected and photoelectrically converted by light receiving means to thereby obtain image information on the eye, comprising:
- non-mechanical optical scanning means for scanning a laser beam from a laser light source in one direction at a prescribed frequency;
- two mirror galvanometers for scanning the laser beam perpendicularly and parallel to the scanning direction of the non-mechanical optical scanning means at two frequencies that are lower than above said frequency;
- light receiving means for detecting and photoelectrically converting light from the two mirror galvanometers reflected by the eye, via a prescribed detection aperture;
- control means that performs angle of view conversion by changing the laser beam deflection angle of the three optical scanning means; and
- signal processing means for converting a detection signal obtained from the light receiving means to a standard television vertical and horizontal scanning line system corresponding to a laser beam scanning pattern obtained with the three optical scanning means.

43. A scanning laser ophthalmoscope according to claim 42, in which the detection aperture is located at a position that is optically conjugate with the laser beam focal point in the eye, and is formed in a prescribed shape around a region in which the laser beam focal point moves in accordance with the laser beam scanning pattern of the optical scanning means.

44. A scanning laser ophthalmoscope according to claim 42 in which the laser beam scanning pattern formed by all of the optical scanning means is a two-dimensional zig-zag pattern formed by scanning the laser beam in a second direction perpendicular to a first scanning direction while the beam makes small oscillations along the first scanning direction, and scanning the laser beam in a third direction parallel to the first scanning direction.

45. A scanning laser ophthalmoscope according to claim 42, in which the signal processing means for converting a detection signal obtained from the light receiving means to a standard television scanning line system consists of an A/D converter for performing analogue-to-digital conversion of the detection signal, a memory for storing digital data output by the A/D converter, control means for controlling the writing of data to, and readout of data from, the memory, and a D/A converter for performing digital-to-analogue conversion of digital data read out of the memory.

46. A scanning laser ophthalmoscope according to claim 42, further comprising optical focal adjustment means for moving the laser beam focal point in the eye.

47. A scanning laser ophthalmoscope according to claim 46, in which the focus adjustment means is a slanted lens that can be moved along the path of the laser beam.

48. A scanning laser ophthalmoscope in which a laser beam from a laser light source is projected onto a prescribed part of an eye and scanned in two dimensions, and light reflected from the eye is detected and photoelectrically converted by light receiving means to thereby obtain image information on the eye, comprising:
- a laser diode array with optical scanning capability as a laser light source for generating laser beams of one or multiple frequencies and scanning the emitted laser beams in one direction at a prescribed frequency;
- two mechanical optical scanning means for scanning the laser beam perpendicularly and parallel to the scanning direction of the laser diode array at two frequencies that are lower than above said frequency;
- light receiving means constituted by a photodiode array for detecting and photoelectrically converting light from the mechanical optical scanning means reflected by the eye; and
- signal processing means for converting a detection signal obtained from the light receiving means to a standard television vertical and horizontal scanning line system corresponding to a laser beam scanning pattern obtained with the laser diode array and two mechanical optical scanning means.

49. A scanning laser ophthalmoscope according to claim 48, in which the laser beam scanning pattern formed by all of the optical scanning means is a two-dimensional zig-zag pattern formed by scanning the laser beam in a second direction perpendicular to a first scanning direction while the beam makes small oscillations along the first scanning direction, and scanning the laser beam in a third direction parallel to the first scanning direction.

50. A scanning laser ophthalmoscope according to claim 48, in which the signal processing means for converting a detection signal obtained from the light receiving means to a standard television scanning line system consists of an A/D converter for performing analogue-to-digital conversion of the detection signal, a memory for storing digital data output by the A/D converter, control means for controlling the writing of data to, and readout of data from, the memory, and a D/A converter for performing digital-to-analogue conversion of digital data read out of the memory.

51. A scanning laser ophthalmoscope according to claim 48, further comprising optical focal adjustment means for moving the laser beam focal point in the eye.

52. A scanning laser ophthalmoscope according to claim 51, in which the focus adjustment means is a slanted lens that can be moved along the path of the laser beam.

* * * * *